US006974430B2

(12) United States Patent
Evans

(10) Patent No.: US 6,974,430 B2
(45) Date of Patent: Dec. 13, 2005

(54) KNITTED SUBSTRATE WITH HIGH AND LOW TENACITY YARNS FOR USE IN BANDAGING PRODUCT, BANDAGING PRODUCT AND METHOD OF FORMING SAME

(75) Inventor: John C. Evans, Nr Rochdale (GB)

(73) Assignee: ESN Medical, Inc., Wilmington, DE (US)

( * ) Notice: Subject to any disclaimer, the term of this patent is extended or adjusted under 35 U.S.C. 154(b) by 0 days.

(21) Appl. No.: 10/348,139

(22) Filed: Jan. 21, 2003

(65) Prior Publication Data

US 2004/0024338 A1 Feb. 5, 2004

Related U.S. Application Data

(60) Provisional application No. 60/401,086, filed on Aug. 5, 2002.

(51) Int. Cl.[7] ................................................. A61F 5/00
(52) U.S. Cl. ............................................. 602/8; 602/6
(58) Field of Search ................................ 602/5, 6, 8, 3

(56) References Cited

U.S. PATENT DOCUMENTS

| 2,761,443 | A |   | 9/1956  | Parker       |
|-----------|---|---|---------|--------------|
| 2,960,984 | A |   | 11/1960 | Parker       |
| 3,683,903 | A |   | 8/1972  | Fox          |
| 4,235,228 | A |   | 11/1980 | Gaylord, Jr. |
| 4,411,262 | A |   | 10/1983 | von Bonin    |
| 4,427,002 | A |   | 1/1984  | Baron        |
| 4,572,171 | A |   | 2/1986  | Wegner       |
| 5,003,970 | A |   | 4/1991  | Parker       |
| 5,403,267 | A | * | 4/1995  | Pearce et al. ................... 602/8 |
| 6,030,355 | A | * | 2/2000  | Callinan et al. ................ 602/6 |
| 6,290,663 | B1| * | 9/2001  | Darcey ........................... 602/8 |

OTHER PUBLICATIONS

Parker Medical Associates, The first fiberglass splint roll Ortho-Glass, 1988,8 pgs., Parker Medical Asscs, Charlotte, NC.
3M, New Scotchcast 2 Splinting System, 10 pgs., Orthopedic Products Division/3M, St. Paul, MN.
Cutter Laboratories, Inc.,From the Makers of Cuttercast Casting Tape, Jan. 1982, 4 pgs., Cutter Biomedical, Emeryville CA.
Zimmer, Inc., Do You Always Wind Up In A Mess With Splints?, 1986, 7 pgs., Patient Care, Charlotte, NC.
Blauvelt, Nelson, MD, FACS, FAAOS, Casts, splints, dressings, and in-house traction, A Manual of Orthopaedic Terminology, 1990, 2 pgs., Fourth Edition, The C.V. Mosby Co., USA.
Carapace, Inc., When the pressure's on, nothing stands up better than EnduraSplint, 1 pg., Carapace, Inc., Tulsa, Oklahoma.

* cited by examiner

Primary Examiner—Kim M. Lewis
(74) Attorney, Agent, or Firm—Adams Evans P.A.

(57) ABSTRACT

A cast tape or medical bandaging product formed from a resin-coated or impregnated fabric material that includes a knitted substrate having a combination of non-fiberglass high and low tenacity yarns such as polypropylene, polyester and elastomer. The polypropylene and polyester yarns have a high number of filaments, typically 48 to 90 filaments. This significantly improves the surface area of the fabric, that helps help to hold the curable resin onto the fabric and avoids pooling. This in turn improves lamination layer-to-layer and gives the substrate high strength.

21 Claims, 14 Drawing Sheets

KNITTED SUBSTRATE WITH HIGH AND LOW TENACITY YARNS FOR USE IN BANDAGING PRODUCT, BANDAGING PRODUCT AND METHOD OF FORMING SAME

TECHNICAL FIELD AND BACKGROUND OF THE INVENTION

This invention relates generally to the field of orthopedic medicine and more specifically to the design of an improved medical bandaging product and material that includes a fabric substrate impregnated with a moisture-curable resin, a method for constructing such an improved bandaging product, and a method of constructing and applying an improved bandaging product. More particularly, the present invention relates to an orthopedic cast tape formed from a resin-coated fabric substrate featuring a unique combination of non-fiberglass high and low tenacity yarns.

Conventional moisture-curable bandages incorporate substrates impregnated with plaster-of-paris or formed from flexible fiberglass fabric layers impregnated with a moisture-curable resin. Bandages formed from these materials possess several disadvantages. In particular, casts formed using plaster-of-paris bandages have a relatively low strength to weight ratio. This results in a finished cast that is very heavy and bulky. Furthermore, plaster-of-paris splints are slow to harden, requiring 24 to 72 hours to reach maximum strength. Because plaster-of-paris breaks down in water, bathing and showering are difficult. Even if wetting due to these causes can be avoided, perspiration over an extended period of time can break down the plaster-of-paris and create a significant problem with odor and itching.

Although medical bandages utilizing moisture-curable substrates formed from fiberglass fabric layers are lighter, waterproof and permeable to X-rays, cured casts made using such bandages can become brittle, break down during wear and often need to be replaced. Furthermore, fiberglass is a composition that is highly irritating to mammalian skin. When fiberglass casts are removed, irritating dust or fibers are often generated and become embedded in the skin of the patient.

This invention overcomes the disadvantages of prior art fiberglass substrates by providing a medical bandage formed from a resin-impregnated substrate formed from a knitted fabric that incorporates low modulus, inelastic and elastic fibers. The unique substrate of the present invention results in a bandage that exhibits good conformability compared to prior art fiberglass substrates, possesses sufficient rigidity when cured, and shows no loss of strength compared to casts formed from fiberglass substrates. This novel substrate is less brittle and more durable than prior art fiberglass substrates when cured, and does not disintegrate into irritating dust and/or fibers when removed from the injured body part of a patient.

As used herein, the terms "fiber" and "yarn", whether appearing in singular or plural form, are used interchangeably and refer to the material that is used to form the substrate of the present invention, regardless of whether that yarn or fiber is formed of monofilament or multifilament fibers.

SUMMARY OF THE INVENTION

It is therefore an object of the invention to provide a medical bandaging product, such as a cast tape, having a substrate formed from elastic fibers and from inelastic fibers, both having a low modulus of elasticity.

It is another object of the invention to provide a medical bandaging product including a medical bandaging material formed from a resin-impregnated substrate formed from knitted elastic fibers and inelastic fibers, both having a low modulus of elasticity.

It is another object of the invention to provide a medical bandage material that can be dispensed in any desired length while preventing hardening of the remaining material until use of the remaining material is desired.

It is another object of the invention to provide a medical bandaging product that can be manufactured and sold in pre-cut lengths, each of which is sealed within a moisture-impervious package to prevent hardening of the product until use is desired.

It is another object of the present invention to provide a novel use of high tenacity synthetic yarns to provide a casting tape that offers improved conformability and moldability with strength equivalent to casting tapes made from fiberglass.

It is another object of the present invention to provide a casting tape that is durable under heavy loading, is breathable, and has a smooth surface as compared to fiberglass cast tapes.

It is another object of the present invention to provide a cast tape having a knitted structure and that utilizes elastomerics in a manner that gives the cast tape excellent conformability.

It is another object of the present invention to provide a cast tape utilizing a non-covered fine elastomeric yarn, that enhances the performance of the tape with respect to "end lay down," whereby the end of the tape does not "creep back" or fail to laminate to other layers when the tape is cut.

It is another object of the invention to provide a medical bandaging material that includes a resin-impregnated substrate formed from knitted non-fiberglass yarns having high and low tenacity.

These and other objects and advantages of the present invention are achieved in the preferred embodiments disclosed below by providing a cast tape or other medical bandaging product formed from a resin-coated or impregnated fabric material that includes a Raschel knitted substrate having a combination of non-fiberglass high and low tenacity yarns such as polypropylene, polyester and elastomer. The polypropylene and polyester yarns have a high number of filaments, typically 48 to 90 filaments. This significantly improves the surface area of the fabric, that helps help to hold the curable resin onto the fabric and avoids pooling. This in turn improves layer-to-layer lamination and gives the substrate high strength.

According to one preferred embodiment of the invention, the medical bandaging product comprises a sleeve of a predetermined length formed of a moisture-impervious material and sealable to prevent entry of moisture, and a medical material positioned within the sleeve in substantially moisture-free conditions and sealed therein against moisture until use. The medical material comprises a substrate having a pair of opposed, major surfaces. The substrate is constructed of an elastomeric yarn to provide the substrate with a predetermined extensibility. A reactive system is impregnated into or coated onto the substrate. The system remains stable when maintained in substantially moisture-free conditions and hardens upon exposure to sufficient moisture to form a rigid, self supporting structure.

According to another preferred embodiment of the invention, the substrate comprises a knitted fabric.

According to yet another preferred embodiment of the invention, the substrate comprises a knitted fabric fabricated from both elastomeric and inelastic yarns.

According to yet another preferred embodiment of the invention, the substrate comprises a knitted fabric having an extensibility of between 40 and 80 percent prior to being coated or impregnated with the reactive system.

According to yet another preferred embodiment of the invention, the sleeve comprises a aluminum foil laminate having an outer tear resistant layer, a central aluminum foil layer and an inner heat sealable plastic layer.

According to yet another preferred embodiment of the invention, the substrate is formed of fibers selected from the group consisting of synthetic elastomeric fibers and rubber.

Preferably, the substrate is warp knitted.

According to yet another preferred embodiment of the invention, the elastomeric fibers are present in the substrate in the warp direction.

According to yet another preferred embodiment of the invention, the reactive system comprises a blended polyisocyanate, polyol, catalyst and stabilizer.

According to yet another preferred embodiment of the invention, the medical bandaging material is formed into a coil.

According to yet another preferred embodiment of the invention, the substrate is elongate and includes a dispensing carton within which the coil of medical bandaging product is contained.

According to yet another preferred embodiment of the invention, an elongate medical bandage is provided, and comprises an elongate medical material adapted for being dispensed in lengths suitable for a given medical use and for being maintained in substantially moisture-free conditions until use. The medical bandage comprises a knitted substrate knitted of elastomeric yarns and defining a pair of opposed major surfaces, and a reactive system impregnated into or coated onto the substrate. The system remains stable when maintained in substantially moisture-free conditions and hardens upon exposure to sufficient moisture to form a rigid, self supporting structure.

According to yet another preferred embodiment of the invention, the substrate comprises a warp knitted fabric.

According to yet another preferred embodiment of the invention, the substrate also includes inelastic yarns.

According to yet another preferred embodiment of the invention, the substrate comprises a knitted fabric having an extensibility of between 40 to 80 percent prior to being coated or impregnated with the reactive system.

According to yet another preferred embodiment of the invention, the medical bandage is packaged until use in a sleeve comprising an aluminum foil laminate having an outer tear resistant layer, a central aluminum foil layer and an inner heat sealable plastic layer.

According to yet another preferred embodiment of the invention, the substrate is formed of fibers selected from the group consisting of synthetic elastomeric fibers and rubber.

According to yet another preferred embodiment of the invention, the substrate includes inelastic fibers selected from the group consisting of polypropylene and polyester.

According to yet another preferred embodiment of the invention, the polypropylene and polyester yarns each have between 48–90 filaments.

According to yet another preferred embodiment of the invention, the reactive system comprises a blended polyisocyanate, polyol, catalyst and stabilizer.

According to yet another preferred embodiment of the invention, the medical bandage is formed into a coil.

According to yet another preferred embodiment of the invention, a dispensing carton is provided within which the coil of medical bandaging product is contained.

According to yet another preferred embodiment of the invention, the substrate is formed of uncovered elastomeric yarns of between 60–150 Decitex.

According to yet another preferred embodiment of the invention, an elongate medical bandaging product is provided for being dispensed in lengths suitable for a given medical use, and comprises an outer container formed of a moisture-impervious material and sealable to prevent entry of moisture. The container comprises an elongate product-dispensing sleeve having a moisture-proof sealable opening on one end and an enlarged product storage package communicating with the dispensing sleeve. An elongate medical material is positioned in the container in substantially moisture-free conditions and sealed therein against moisture until use. The medical material comprises a knitted substrate having a pair of opposed, major surfaces. A reactive system is impregnated into or coated onto the substrate, the system remaining stable when maintained in substantially moisture-free conditions and hardening upon exposure to sufficient moisture to form a rigid, self supporting structure. Closure means are provided for resealing the dispensing sleeve against entry of moisture after a predetermined length of the medical material has been dispensed for use to prevent hardening of the substrate remaining in the product container.

According to yet another preferred embodiment of the invention, the dispensing sleeve and the product storage package are integrally-formed.

According to yet another preferred embodiment of the invention, a protective carton is provided within which the product container is contained.

According to yet another preferred embodiment of the invention, the elongate medical material is coiled within the storage package with an end portion thereof positioned in the product-dispensing sleeve for selective dispensing of desired lengths thereof.

According to yet another preferred embodiment of the invention, the modulus of the yarns used in the resin-coated or impregnated fabric material is greater than 3 centinewtons per Decitex, but between 3 and 30 centinewtons per Decitex.

According to another preferred embodiment of the invention, the fabric material is formed from an uncovered elastomeric yarn of between 60–150 Decitex.

According to yet another preferred embodiment of the invention, the fabric material includes an inlay stitch of polyester yarn between 250–350 Decitex.

According to yet another preferred embodiment of the invention, the polyester yarn employed in the fabric material has a modulus of 3–30 centinewtons.

According to yet another preferred embodiment of the invention, the polypropylene yarn employed in the fabric material has a modulus of 6/30 centinewtons per Decitex.

According to yet another preferred embodiment of the invention, the extension, or elongation, of the polyester and polypropylene yarns employed in the fabric material is between 9–30 percent.

According to yet another preferred embodiment of the invention, the knitted fabric material exhibits an extensibility of 40–80 percent prior to the application of the curable resin to the fabric material.

BRIEF DESCRIPTION OF THE DRAWINGS

Some of the objects of the invention have been set forth above. Other objects and advantages of the invention will appear as the invention proceeds when taken in conjunction with the following drawings, in which:

FIG. 6 is a perspective view of a medical bandaging product according to an alternative embodiment of the invention

DESCRIPTION OF THE PREFERRED EMBODIMENT AND BEST MODE

Figure 1:
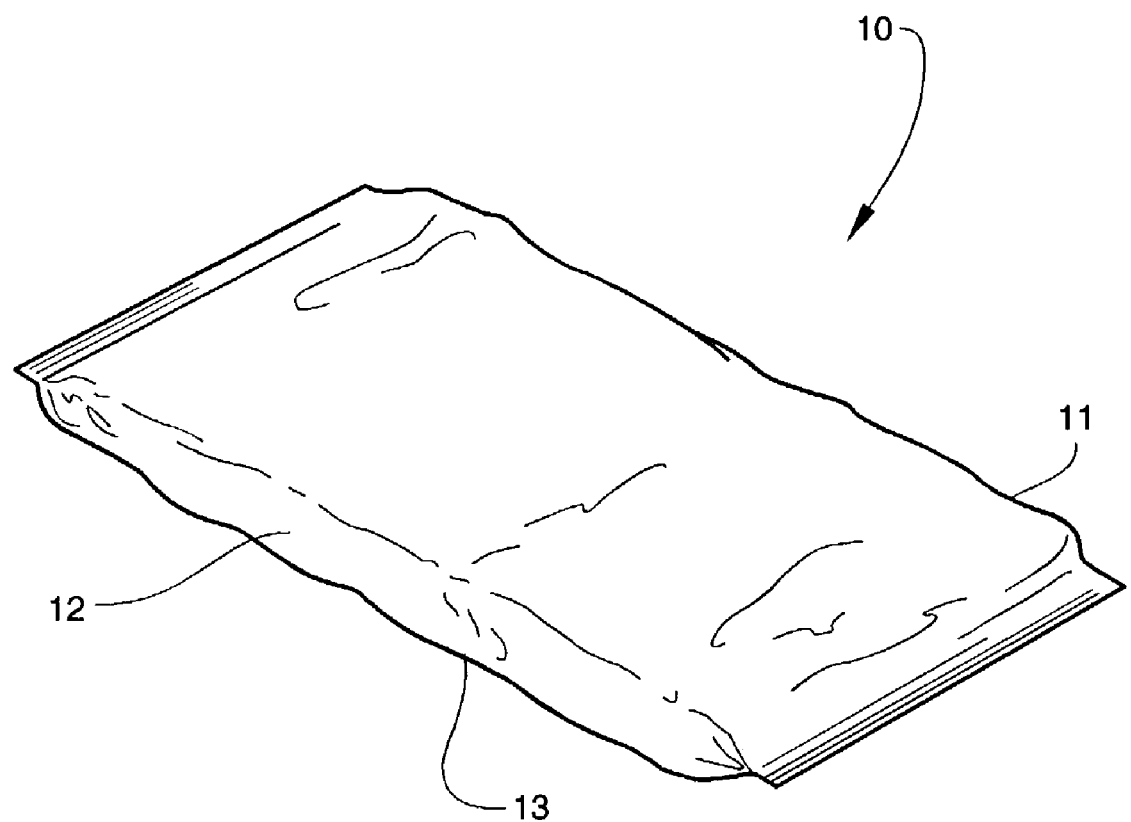
FIG. 1 is a perspective view of a medical bandaging product according to one preferred embodiment of the invention.
Figure 2:
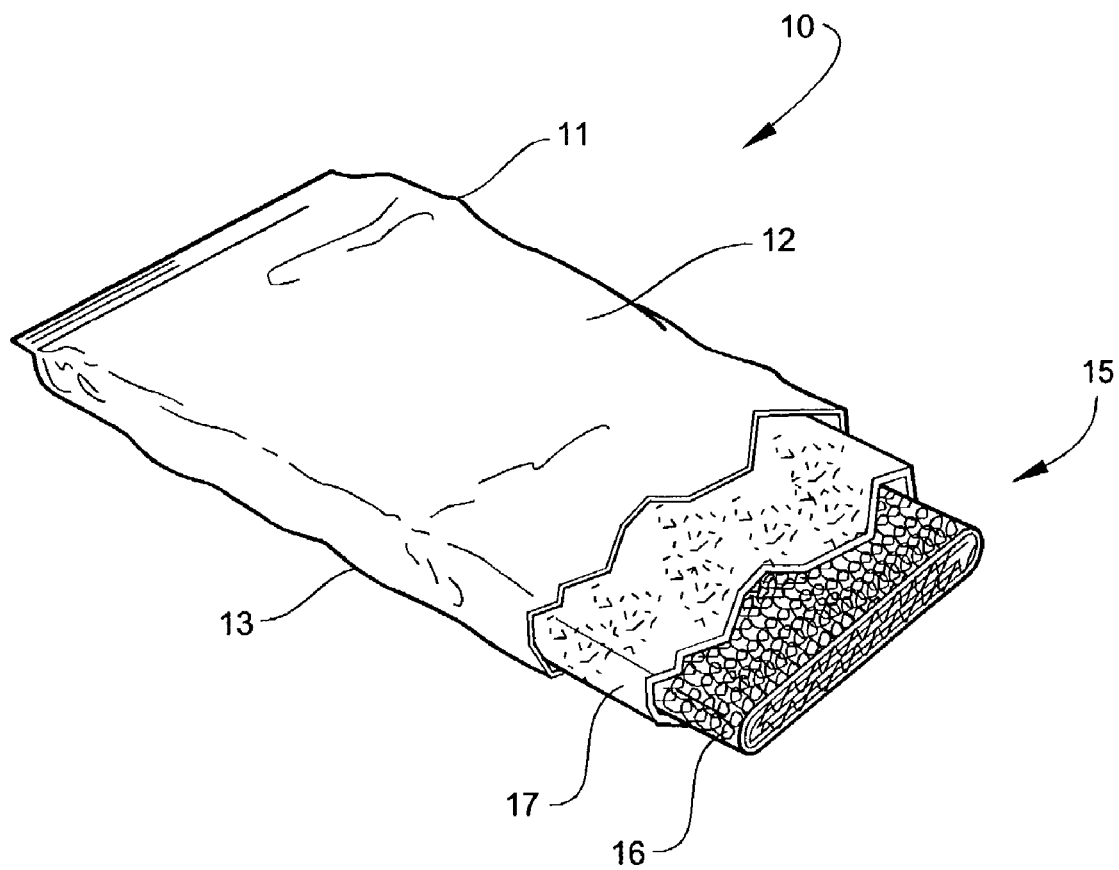
FIG. 2 is a cut-away fragmentary perspective view of the medical bandaging product shown in FIG. 1.

Referring now specifically to the drawings, a medical bandaging product 10 according to the present invention is shown generally in FIG. 1. The medical bandaging product 10 includes a moisture-impervious sleeve 11 formed from two laminated sheets 12 and 13 that are placed in registration and heat sealed along opposite edges. As is shown in FIG. 2, the bandaging product 10 also includes a medical bandage 15 that is maintained in moisture-free conditions within the sleeve 11 until use. The bandage 15 includes a substrate 16. In the embodiment of the invention shown in FIG. 2, the substrate 16 is enclosed within an outer cover 17 formed of a soft, flexible, hydrophobic fiber. However, the bandage 15 may also be formed without the outer cover. As discussed more fully with reference to FIG. 5 below, the substrate 16 is a knitted fabric material formed from elastic and inelastic fibers.

Although any suitable moisture-resistant material may be used to form the sleeve 11 within which the bandage 15 is positioned, the sleeve 11 preferably includes outer, middle, and inner layers. The outer layer is preferably formed of a tear-resistant plastic film. The middle layer is preferably formed from aluminum foil and acts as a moisture resistant barrier for protecting the bandage 15 while stored within the sleeve 11. The inner layer is preferably formed from a plastic film having thermoplastic properties suitable for heat-sealing the interior of the package securely against moisture.

Figure 3:
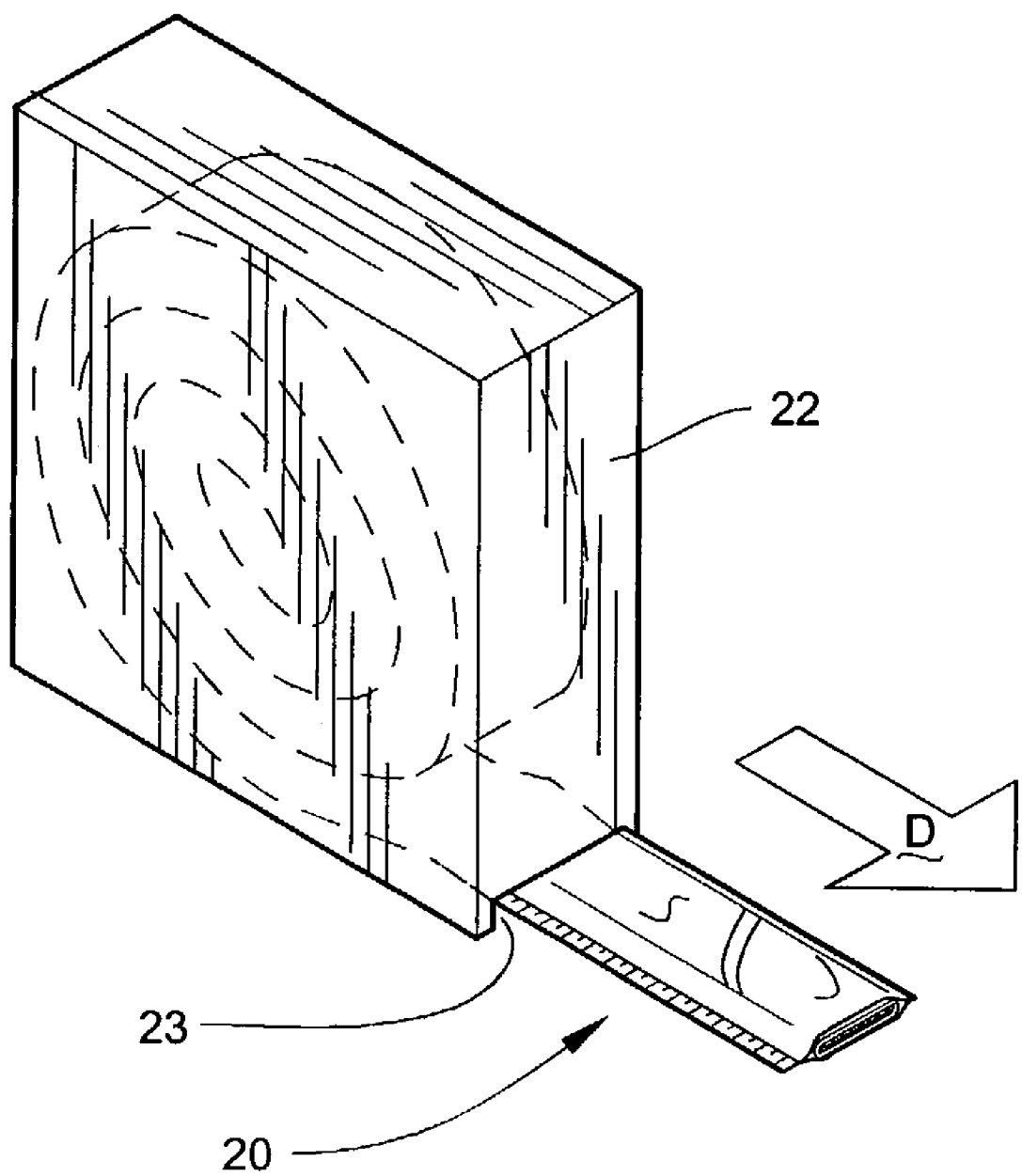
FIG. 3 is a perspective view of a medical bandaging product contained in a dispenser.

Referring now to FIG. 3, a medical bandaging product 20 according to another preferred embodiment of the invention is illustrated and shown. The bandaging product 20 may be sold in any convenient length and is rolled into a coil and positioned within a suitable dispenser 22. Although the bandaging product 20 may be positioned within any suitable dispenser, storage container, package or box, a preferred dispenser is a carton 22, as shown in FIG. 3. The carton 22 is provided with a slot 23 defined in one lower corner through which an end of the bandaging product 20 extends for dispensing the product from the dispenser in the direction "D" shown.

Figure 4:
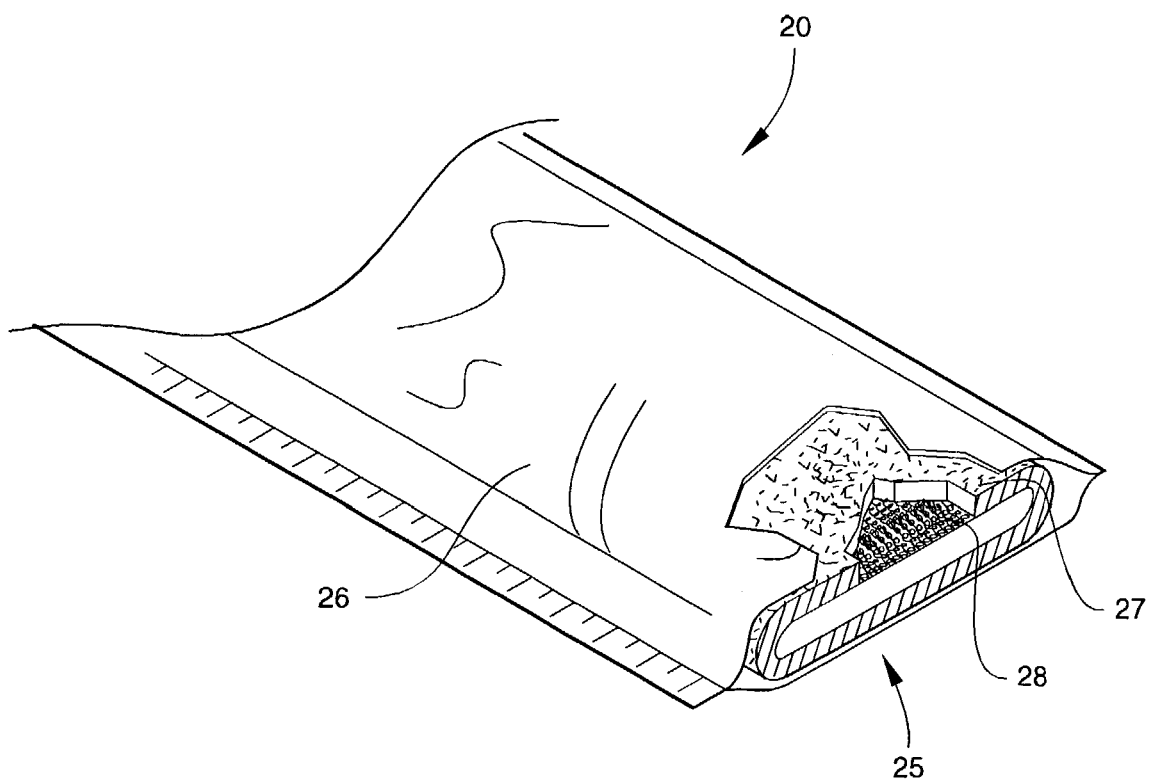
FIG. 4 is a fragmentary perspective view with parts broken away of the medical bandaging material of FIG. 3.

Referring now to FIG. 4, the bandaging product 20 is shown removed from the dispenser 22, and includes an elongate medical bandaging material 25 that is packaged in moisture-free conditions in a foil sleeve 26. The sleeve 26 is formed from two laminated, elongate foil sheets that are placed in registration and heat sealed along opposing side edges to form a tube having an open end. Each sheet is formed from the same materials and includes the same components as the sleeve 11 shown in FIG. 1. The bandage material 25 includes a substrate 28 formed from the same materials and including the same components as the substrate 16 described above with reference to FIG. 2, and discussed in detail below with reference to FIG. 5. While the substrate 28 is shown in FIG. 4 surrounded by a tubular wrapping 27 that protects the skin of a patient from direct contact with the substrate 28 after the bandage material 25 has been applied, the bandage material 25 may alternatively be formed without such a wrapping 27 in the form of a rolled cast tape.

Figure 5:
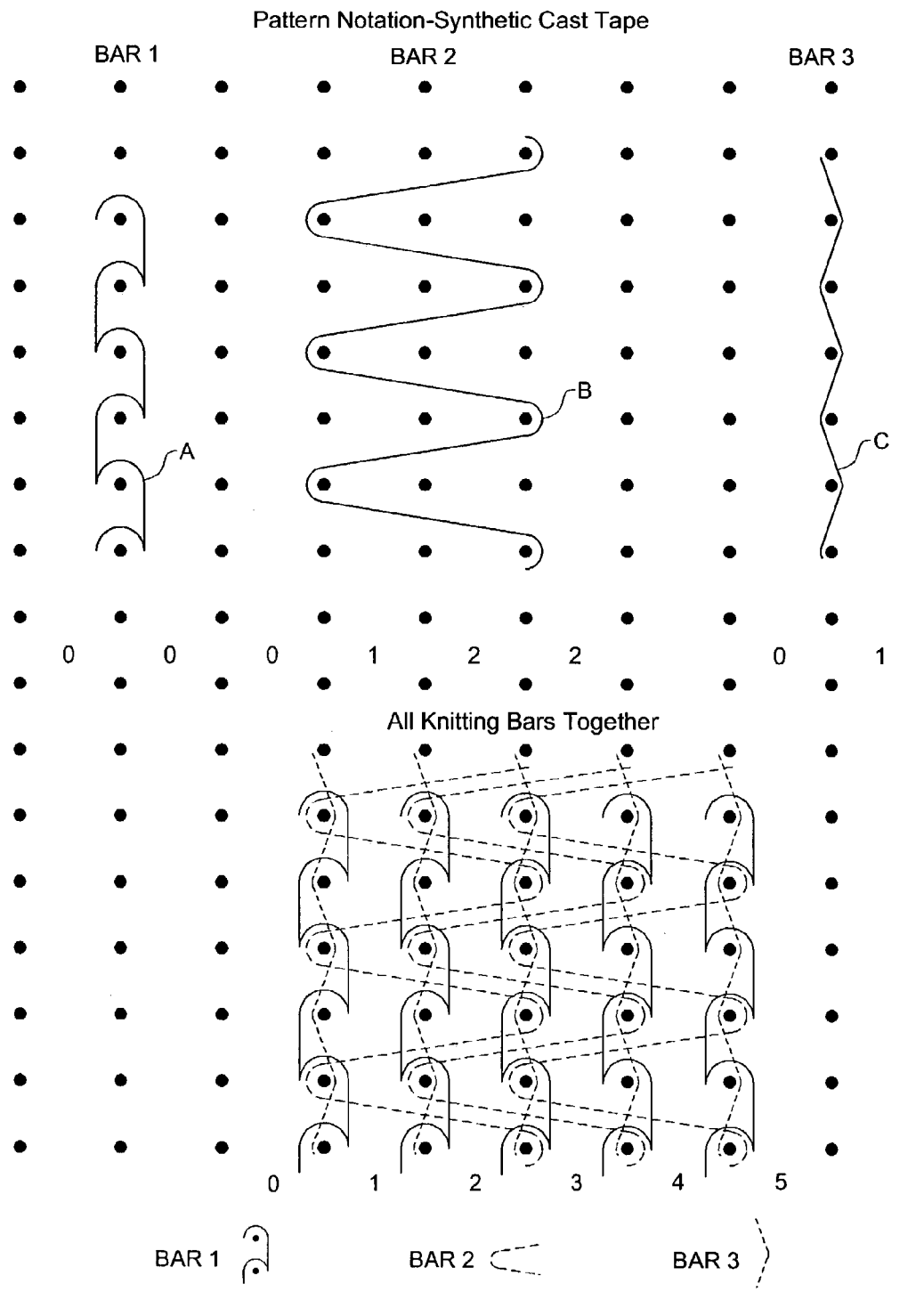
FIGS. 5 and 6 are stitch diagrams showing the stitch pattern used to form the substrate according to the present invention.

Referring now to FIG. 5, the preferred structure of the fabric used to form the substrate 16 and 28 of the present invention is shown. The substrate is a knitted material formed from elastic and inelastic yarns, and preferably exhibits an extensibility of 40 to 80 percent prior to coating or impregnating the substrate with curable resin. The modulus of the yarns is preferably greater than 3 centinewtons per Decitex, and between 3 to 30 centinewtons per Decitex. In one preferred embodiment of the invention, the fabric is formed from an uncovered elastomeric yarn of between 60–150 Decitex.

Although the elastic fibers may be incorporated in any suitable direction along the substrate, the elastic fibers are preferably incorporated along the length of the substrate. This structure permits the substrate to be stretched and extended in the lengthwise direction. The elastic fibers may be formed from any suitable material; however, the elastic fibers are preferably lycra, spandex or polyester fibers such as those sold under the trade name T400 by DuPont. Other suitable elastic fibers may include, but are not limited to, those formed from rubber or elastomeric polymers that have high extendibility and exhibit substantially complete and rapid elastic recovery. Such fibers include those formed from natural rubber or a synthetic elastomer such as polyisoprene, polybutadiene, copolymers of a diene and styrene or acrylonitrile, polychloroprene or copolymers thereof, elastomeric ethylenepropylene copolymers and thermoplastic elastomers including block copolymers of styrene and butadiene or isoprene or an elastic polyurethane yarn. In one preferred embodiment of the invention, the elastic fiber is present in the knitted substrate in the warp (machine) direction.

The inelastic fibers incorporated into the substrate of the present invention are preferably ones having a low modulus of elasticity. Such inelastic fibers include, but are not limited to, polymer fibers such as polypropylene, polyester, polyamide and polyethylene. One preferred fiber is formed from polypropylene and may be employed as a multifilament or monofilament fiber. Another preferred fiber is polyester. Such a polyester fiber includes but is not limited to multifilament or monofilament polyethylene terephthalate fiber. One preferred combination of inelastic fibers is one in which both polypropylene and polyester yarns are used. The use of such inelastic fibers provides particularly durable casts.

Although the polyester and polypropylene yarns may have any number of filaments, the polyester and polypropylene yarns preferably have a high number of filaments, such as between 48 to 90 filaments. Utilizing polyester and polypropylene yarns having such high numbers of filaments improves the surface area of the resultant knitted substrate and enhances the ability of the substrate to absorb and retain the curable resin on the surface or within the interior of the substrate. Using polyester and polypropylene yarns with such a high number of filaments further decreases the likelihood that the resin will pool on the surface of the substrate, that in turn improves lamination of the resin from one layer of the substrate to another within a single medical bandage and significantly improves the strength of the bandage.

Although the polyester yarn may be incorporated into the knitted substrate using any suitable stitch, an inlay stitch of polyester yarn of between 250 to 350 Decitex is preferred. The polyester yarn also preferably has a modulus of 3–30 centinewtons, but may alternatively have a different modulus. The polypropylene yarn may also have any suitable modulus, but preferably has a modulus of between 6–30 centinewtons per Decitex. Furthermore, while the polyester and polypropylene yarns may have any extension, the polyester and polypropylene yarns preferably have an extension (elongation) of between 9–30 percent.

As is shown in FIG. 5, the substrate of the present invention is preferably a Raschel knitted substrate, and is knitted on a knitting machine employing three guide bars. These guide bars are shown in the stitch diagram illustrated in FIG. 5 as Bar 1, Bar 2 and Bar 3, respectively. Three yarns, yarns A, B and C, are threaded on Bar 1, Bar 2 and Bar 3, respectively. Yarns A, B and C are each selected from one of the elastic or inelastic yarns described above, and are preferably polypropylene, polyester and elastomeric yarn.

While the yarns employed in the substrate may be covered or uncovered, in one preferred embodiment of the invention, the substrate is formed from an uncovered elastomeric yarn of between 60–150 Decitex. The substrate may have any suitable thickness and any weight per unit area. Although the fabric of the substrate is preferably a Raschel knit, any suitable knit may be utilized, including but not limited to a crochet knit or tricot knit. Furthermore, the substrate may be a mesh having openings extending therethrough to enable the source of moisture applied during the curing process (see FIGS. 12 and 13 below) to penetrate into the substrate 16, 28 and contact all parts of the resin. The openness of the substrate will also permit circulation of air to and evaporation of moisture from the skin of the patient that is covered by the cured bandage. Although the substrate may be formed from a single layer, the substrate is preferably formed of multiple overlaid fabric layers, for example, from three to seven overlaid layers. Each layer may have a different width and/or length.

The resin used in the embodiments of the present invention may be any curable moisture or water-curable resin that will satisfy the functional requirements of an orthopedic cast. Such resins include, but are not limited to, those disclosed in U.S. Pat. Nos. 4,667,661, 4,502,479, 4,574,793, 4,433,680, 4,427,002, 4,411,262, 3,932,526, 3,908,644, 3,630,194, in German Offenlegungsschrift No. 2651089 and in European Patent Applications Nos. 35517, 57988, 86621 and 94222. The resin used to coat or impregnate the fiber substrate may also be a water curable isocyanate terminated prepolymer system such as those identified in U.S. Pat. Nos. 4,427,002, 4,433,680 and 4,574,793.

One preferred resin used to coat or impregnate the fabric layer or layers of the substrate a moisture-curable resin such as polyisocyanate. This resin is described in full in the present applicant's U.S. Pat. No. 4,770,299. The resin is synthesized using a reactive system that remains stable when maintained in substantially moisture-free conditions, yet hardens upon exposure to sufficient moisture to form a rigid, self-supporting structure. A typical formation of the reactive system is as follows:

| Typical Formulation | | | |
| --- | --- | --- | --- |
| Isonate 143L | or | | 50.0% |
| Mondur CD | or | polyisocyanate | |
| Rubinate Xl68 | | | |
| Pluracol P1010 | | polyol | 46.6% |
| DC-200 Silicone | | defoaming agent | 0.30% |
| Benzoyl Chloride | | stabilizer | 0.10% |
| Thancant↓ DM-70 | | catalyst | 3.0% |
| | | | 100% |

A complete discussion of the parameters of the reactive system, the manner of production and the variables that apply are found in U.S. Pat. No. 4,411,262.

The polyisocyanate resin remains in a viscous state as long as the resin is not exposed to moisture. This permits the substrate to remain flexible and moldable so long as the resin is not exposed to moisture, and for a short period of time after such exposure occurs. The rate at which the resin cures can be controlled to some extent by the quantity of water to which the resin is exposed. Briefly immersing the resin in water will cause the resin to rapidly cure. In contrast, merely exposing the resin to open air will result in a curing process having a significantly slower reaction rate proportional to the amount of moisture in the air to which the resin is exposed.

Figure 6:
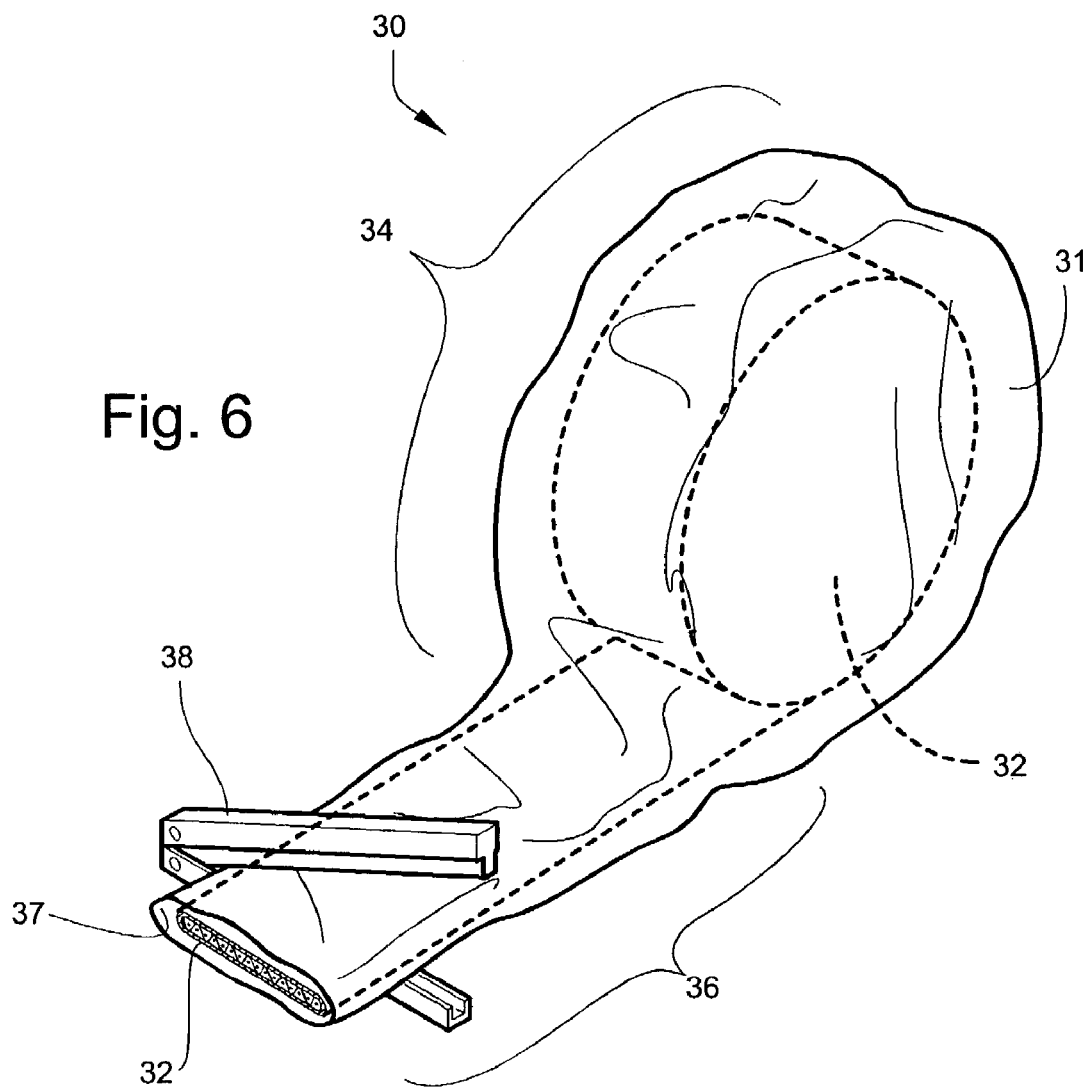
Figure 7:
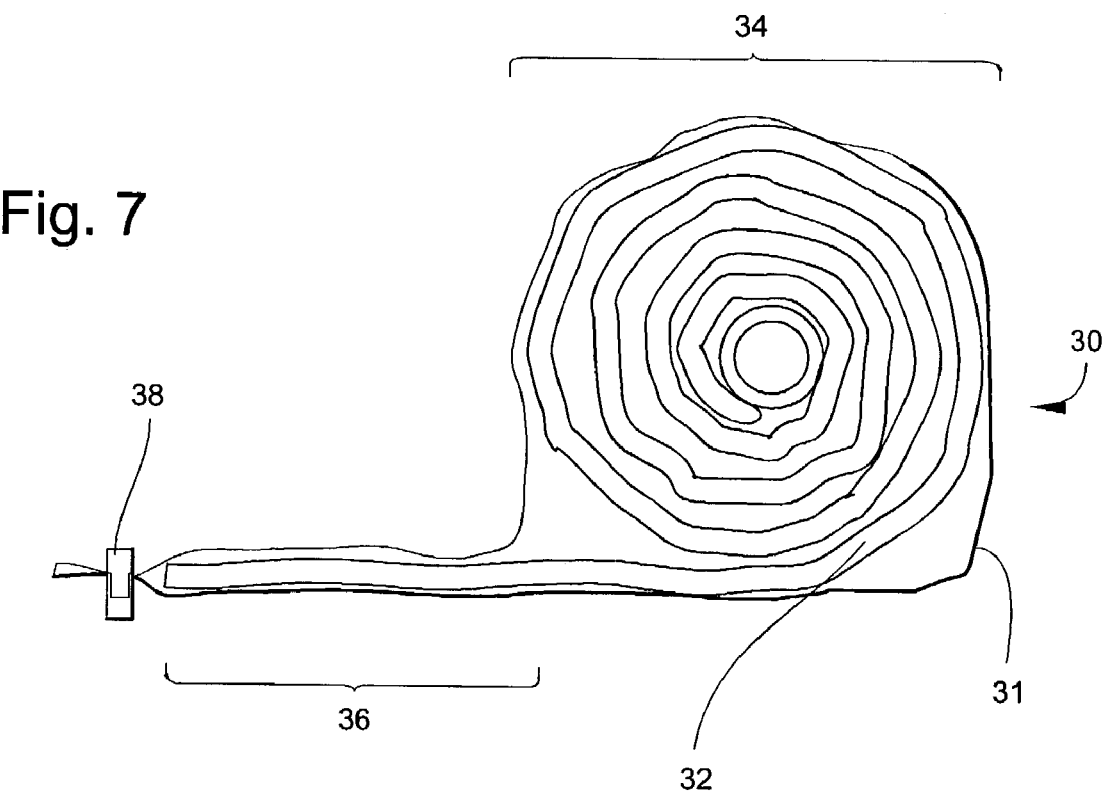
FIG. 7 is a side view of the medical bandaging product shown in FIG. 6 with the clip in a closed position.

Referring now to FIG. 6, an alternative medical bandaging product 30 is illustrated. The bandaging product 30 includes a moisture-impervious foil bag 31 within which is contained a desired length of coiled medical bandaging material 32. The coiled bandaging material 32 includes the same components and is formed from the same materials as the bandaging material 15 described above with reference to FIGS. 1 and 2. The substrate of the coiled bandaging material is identical to that described above with reference to FIG. 5. The foil bag 31 is constructed from the same laminated foil material used to form the sleeve 11 described above with reference to FIG. 1. As is shown in FIG. 6, the bag 31 includes an enlarged 34 enclosure within which the medical bandaging material 32 is contained, and an elongate dispensing sleeve 36. The dispensing sleeve 36 defines an open end 37 through which an end of the medical bandaging material 32 is extended for dispensing. The bag 31 should relatively snugly surround the medical bandaging material 32 to retard entry of moisture into the bag 31 as the material 32 is being dispensed through the open end 37. The open end 37 of the dispensing sleeve 36 may be sealed by means of a clamp 38, shown in its closed position in FIG. 7.

Figure 8:
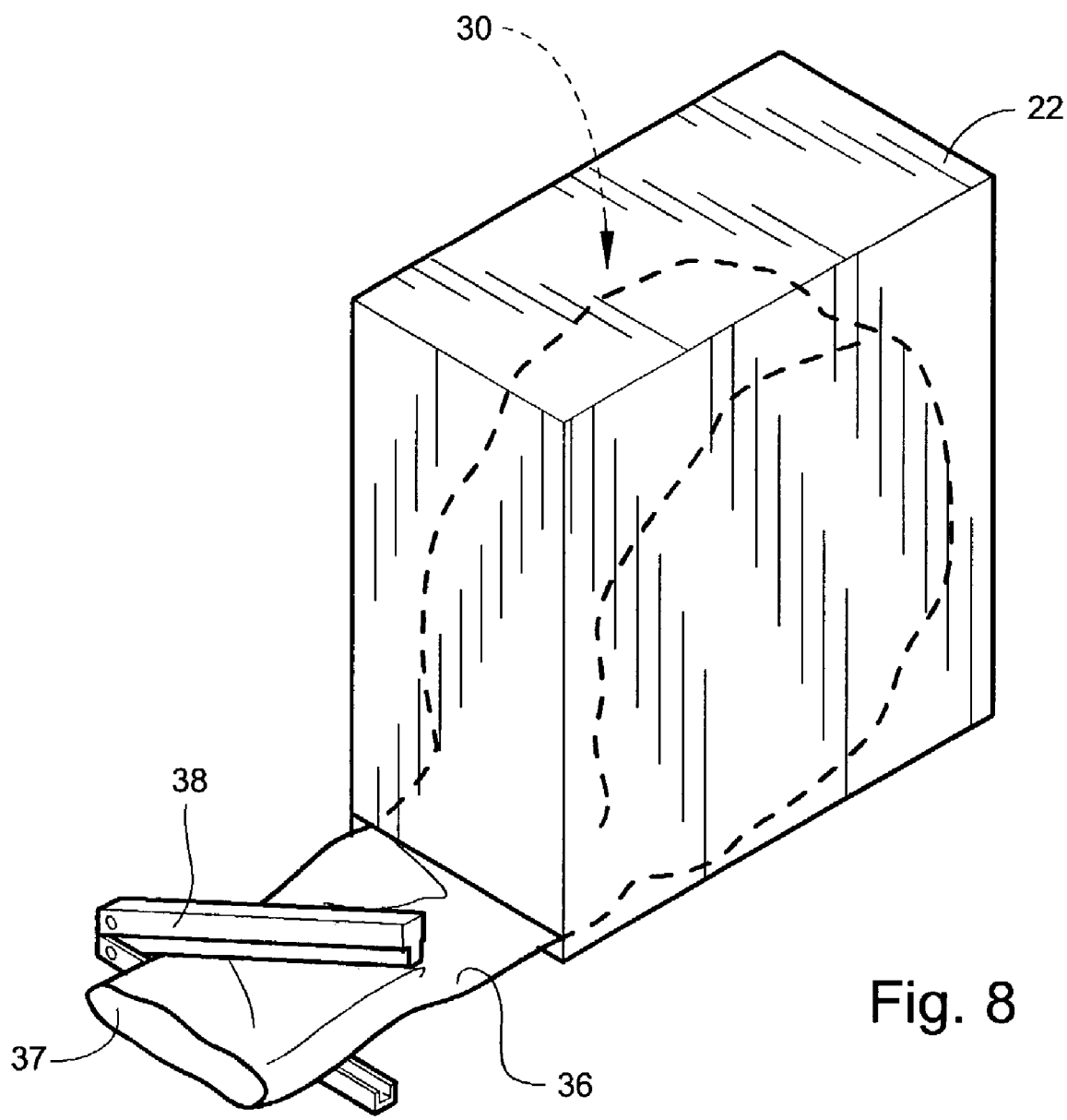
FIG. 8 is a perspective view of the medical bandaging product shown in FIGS. 6 and 7 in a dispensing box.

Referring now to FIG. 8, the bandaging product 30 is shown positioned in a suitable dispenser 22, as described above in reference to FIG. 3.

Figure 9:
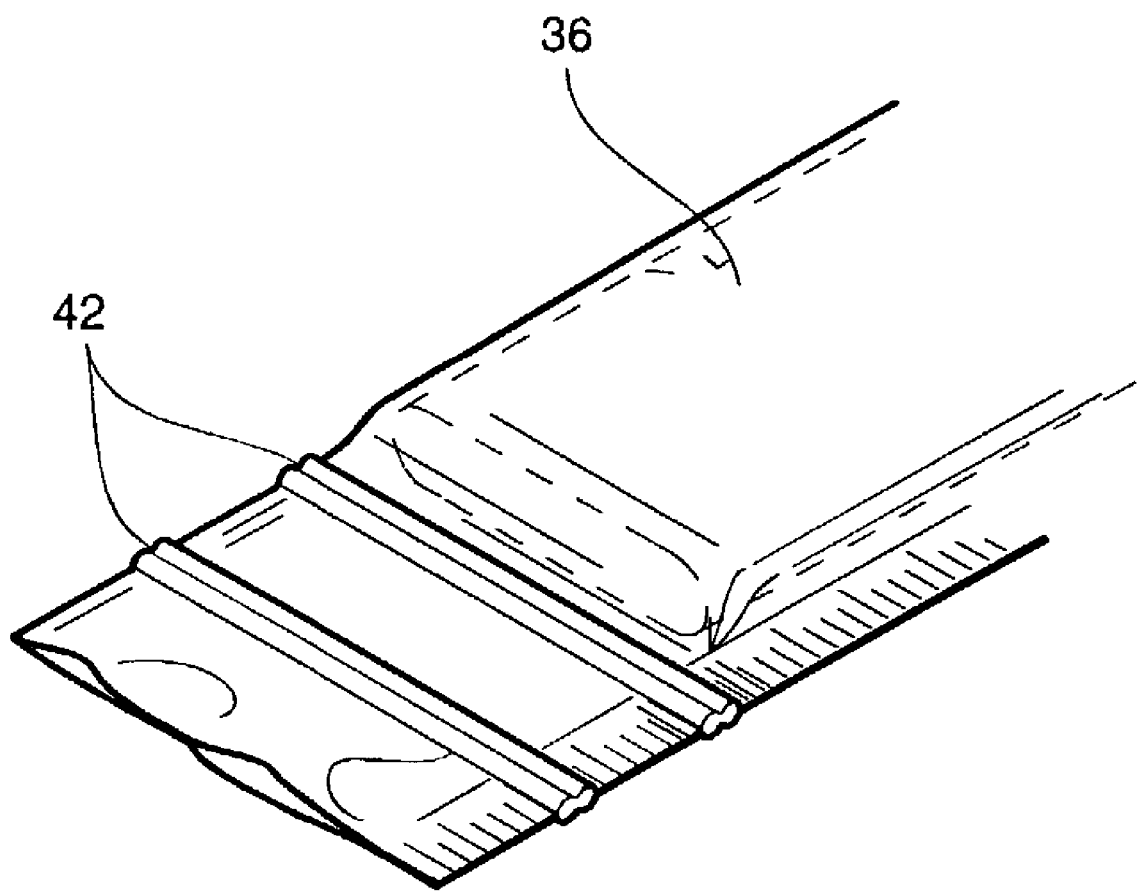
FIG. 9 is a fragmentary perspective view of one embodiment of the medical bandaging product with a zip end closure.
Figure 10:
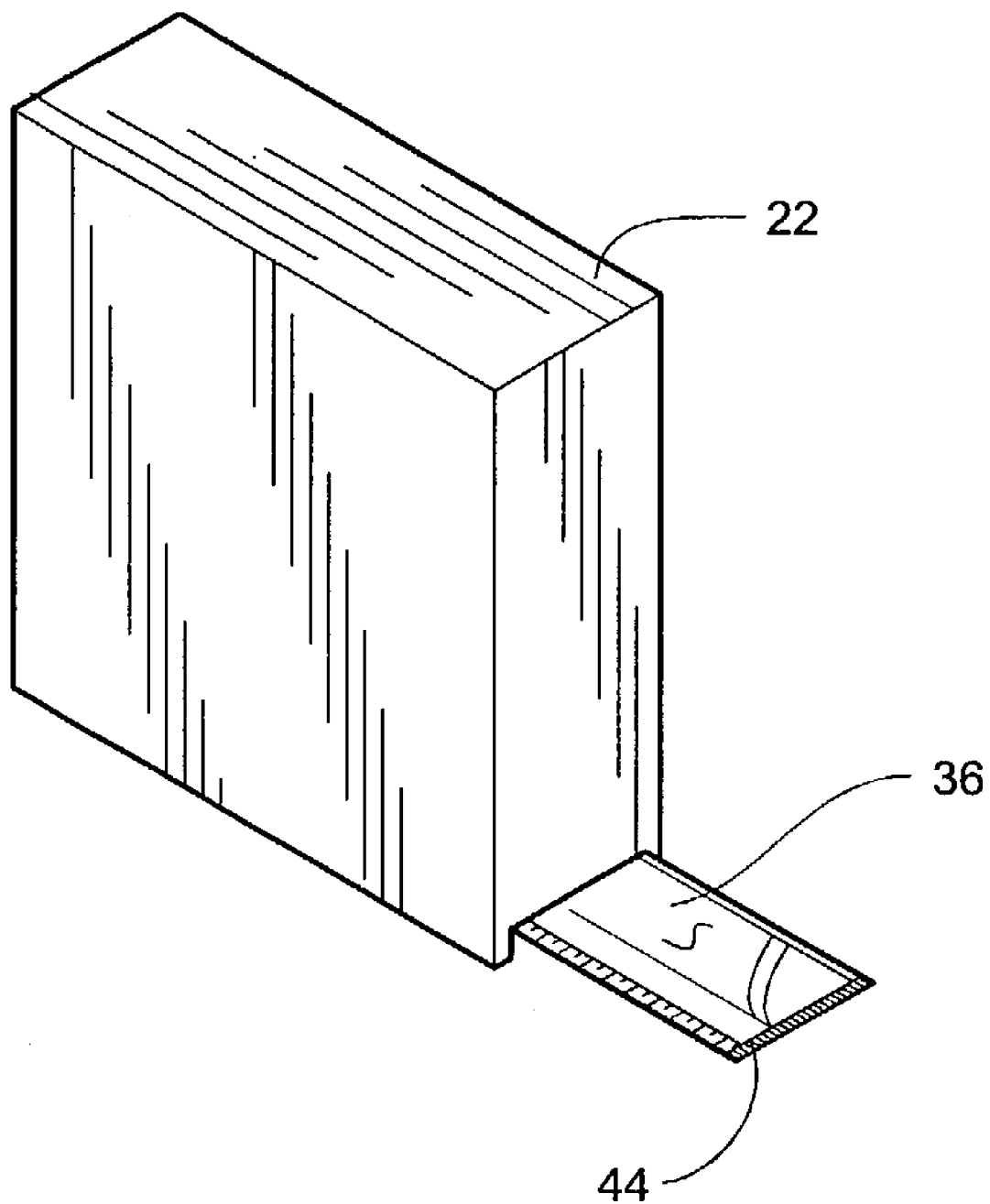
FIG. 10 is a perspective view of the medical bandaging product according to FIG. 6 showing an alternative preferred embodiment of resealing the medical bandaging product.
Figure 11:
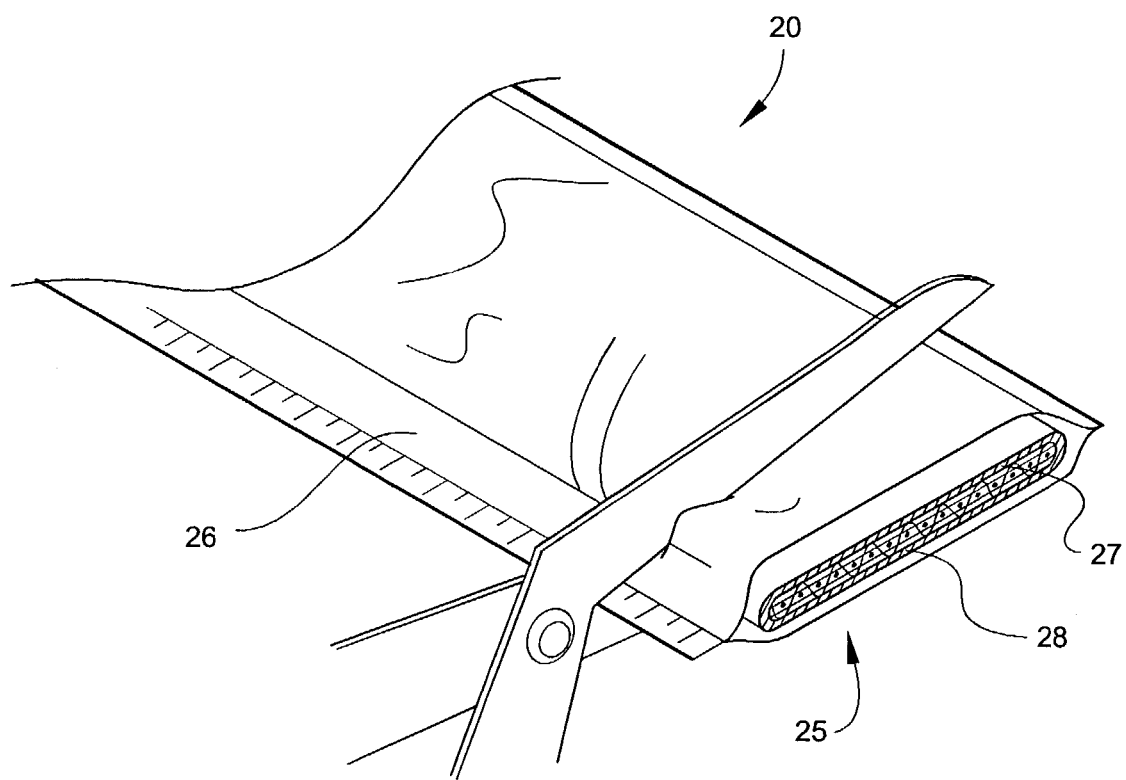
FIGS. 11–15 illustrate a preferred manner of preparing and applying the medical bandage material according to the present invention.

Referring now to FIGS. 9 and 10, alternative sealing means that may be used to seal the end of the dispensing sleeve 36 include zip-type closures as shown in FIG. 9, or a tape strip 44 such as that shown in FIG. 10. The clamp 38, zip-type closure 42 and tape strip 44 may also be used to close the open end of the foil sleeve of the bandaging products 10 and 20 described above.

Other types of sealing mechanisms may also be employed to close the sleeves such as, for example, a clip for holding a folded end of the sleeve closed. A soft, conformable gasketing device may alternatively be used. Such a gasketing device would include spring loaded compression, leverage clamping or screw action of sufficient strength to prevent entry of moisture into sleeve. Another suitable device for sealing the sleeve is a pair of spring loaded rollers. Such rollers roll backwards slightly when compressed, that would in turn push medical bandage material back slightly into respective sleeves, thereby forming a better seal. Another alternative sealing means is one that pushes the medical bandage material back into respective sleeves a sufficient distance (approximately one inch), so that the open ends may be heat sealed.

Referring now to FIGS. 11 through 15, preparation and application of the medical bandaging material 25 of the present invention is illustrated. Using the medical bandage product 20 in FIG. 4 as a representative example, the medical bandaging product 20 is first measured and cut to length using scissors or a knife. Once the appropriate length of product 20 has been cut, the bandaging material 25 is removed from within the foil sleeve 26. The foil sleeve 26 must be immediately resealed to prevent moisture intrusion that can harden the remaining material. See FIGS. 6 through 10.

Figure 12:
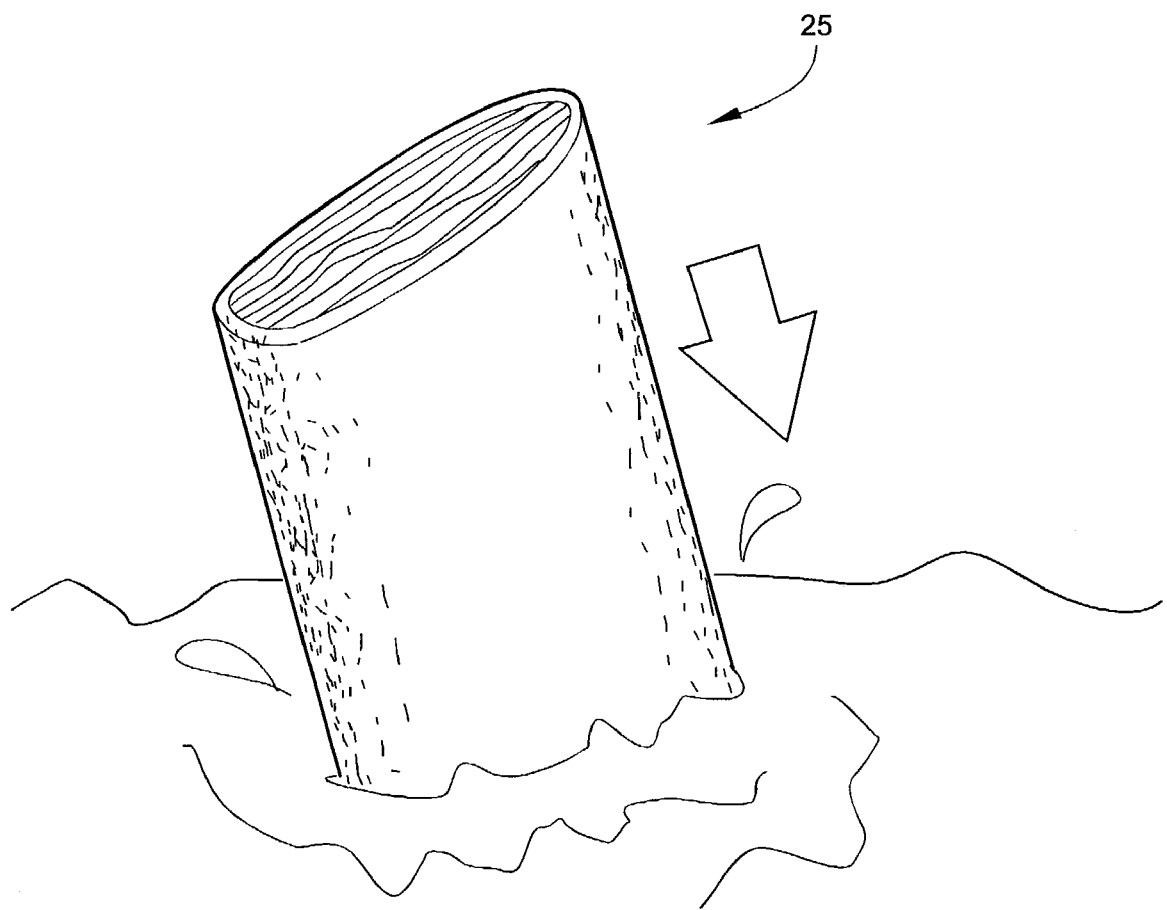
Figure 13:
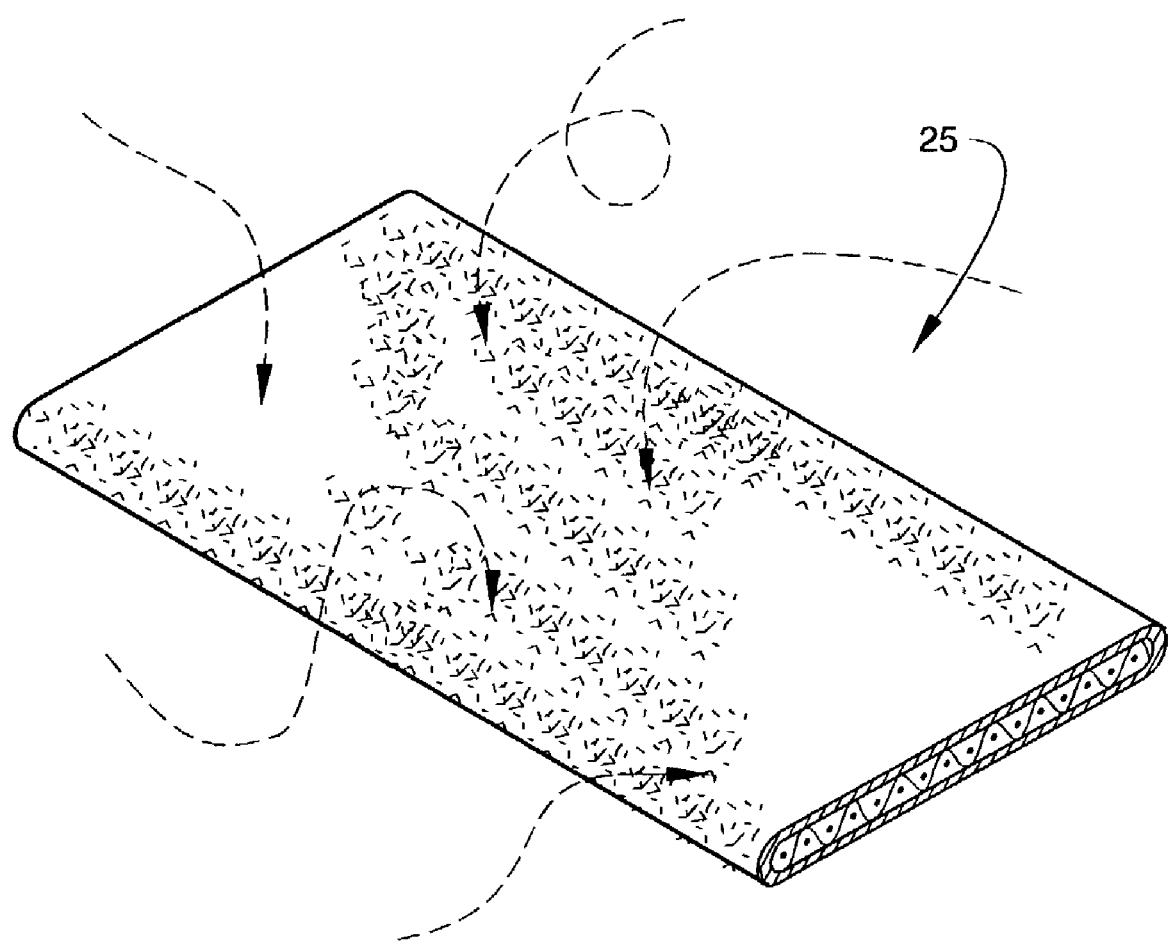

Referring now to FIG. 12, moisture curing of the resin is activated by immersing the medical bandage material 25 in water. The curing process may alternatively be activated by spraying the bandage material 25 with water. Excess moisture is then removed from the material 25 by either squeezing the material or rolling the material in an absorbent towel. As is shown in FIG. 13, the moisture-curing process can alternatively take place over a longer period of time by exposing the reactive system of the bandaging material 25 to atmospheric moisture.

Figure 14:
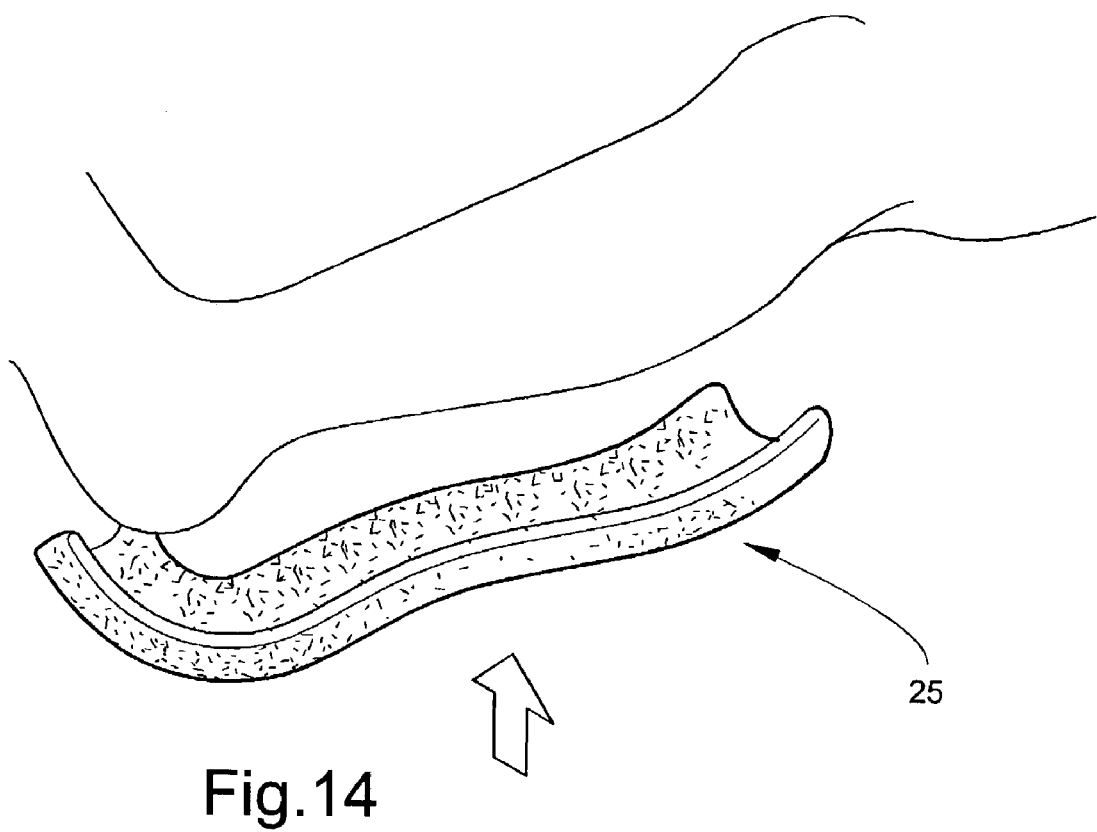
Figure 15:
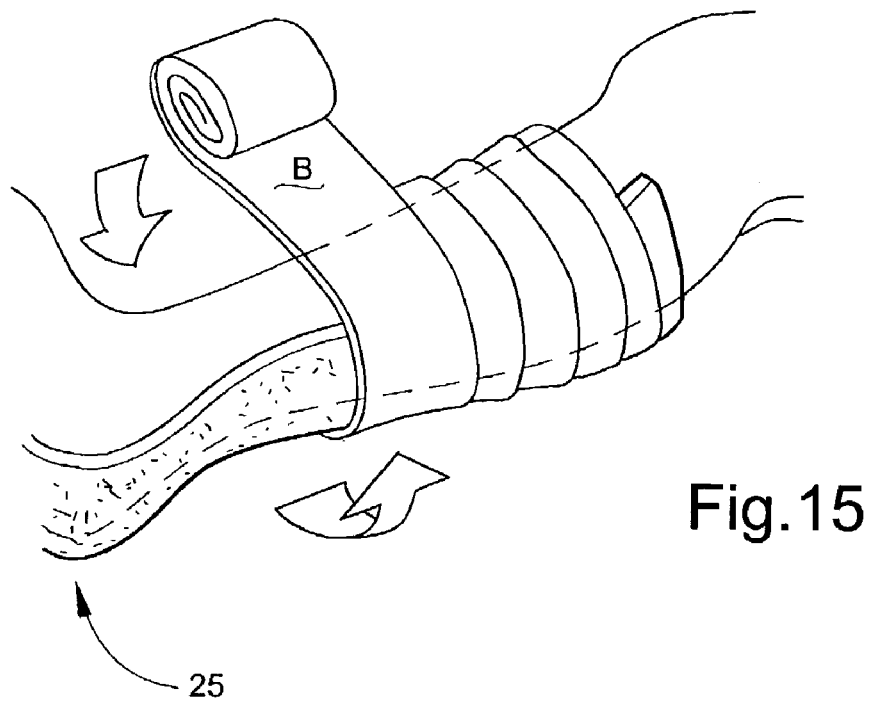

Referring now to FIGS. 14 and 15, a splint commonly known as a posterior short leg splint, and is formed by molding a length of the medical bandage 25 along the calf, over the Achilles's tendon and heel, and onto the foot. As is shown in FIG. 14, an appropriate length of moistened medical bandage material 25 is first formed to the shape of a body member to be immobilized. Once the material 25 is formed to the shape of the body member, the material 25 is overwrapped with a conventional elastic bandage "B", as is shown in FIG. 15.

Although the medical bandage material of medical bandage product is shown in FIGS. 14 and 15 in use as a posterior short leg splint, the medical bandage may be utilized in any suitable medical procedure where immobilization of one or more body members is required. As noted above, the substrate 16 or 28 may be used as cast tape without any overlying protective layer. The ability to elongate enhances the ability of the substrate in cast tape form to closely adhere to the contours of the body part being protected.

As described above, the substrate without any form of cover or protective wrapping can be used as cast tape, in which case the tape would be wrapped circumferentially around the injured limb with a protective material positioned between the limb and the cast tape.

A medical bandaging product and material formed of a moisture-curable plastic material, a method for constructing such an improved medical bandage, and a method of constructing and applying an improved bandaging product is described above. Various details of the invention may be changed without departing from its scope. Furthermore, the foregoing description of the preferred embodiment of the invention and the best mode for practicing the invention are provided for the purpose of illustration only and not for the purpose of limitation—the invention being defined by the claims.

I claim:

1. A medical bandaging product, comprising:
   (a) a sleeve of a predetermined length formed of a moisture-impervious material and sealable to prevent entry of moisture;
   (b) a medical material positioned within the sleeve in substantially moisture-free conditions and sealed therein against moisture until use, said medical material comprising:
   (I) a warp-knitted substrate having a pair of opposed, major surfaces, said substrate being constructed of both elastomeric and inelastic yarns, wherein the elastomeric yarns are present in the warp direction only to provide the substrate with a predetermined extensibility and wherein the elastomeric and inelastic yarns each have about 48 to about 90 filaments; and
   (ii) a reactive system impregnated into or coated onto said substrate, said system remaining stable when maintained in substantially moisture-free conditions and hardening upon exposure to sufficient moisture to form a rigid, self supporting structure.

2. A medical bandaging product according to claim 1, wherein said substrate comprises a knitted fabric having an extensibility of between 40 and 80 percent prior to being coated or impregnated with the reactive system.

3. A medical bandaging product according to claim 1 or 2, wherein said sleeve comprises a aluminum foil laminate having an outer tear resistant layer, a central aluminum foil layer and an inner heat sealable plastic layer.

4. A medical bandaging product according to claim 1, wherein said elastomeric yarns are formed of fibers selected from the group consisting of synthetic elastomeric fibers and rubber.

5. A medical bandaging product according to claim 1, wherein said reactive system comprises a blended polyisocyanate, polyol, catalyst and stabilizer.

6. A medical bandaging product according to claim 1, wherein said sleeve is formed into a coil.

7. A medical bandaging product according to claim 6, wherein the substrate is elongate and includes a dispensing carton within which the coil of medical banding product is contained.

8. An elongate medical bandage, comprising:
   (a) an elongate medical material adapted for being dispensed in lengths suitable for a given medical use and for being maintained in substantially moisture-free conditions until use, said medical bandage comprising:
   (i) a warp knitted substrate knitted of elastomeric and inelastic yarns and defining a pair of opposed major surfaces, wherein the elastomeric yarns are present in the warp direction only and wherein the elastomeric and inelastic yarns each have about 48 to about 90 filaments; and (ii) a reactive system impregnated into or coated onto said substrate, said system remaining stable when maintained in substantially moisture-free conditions and hardening upon exposure to sufficient moisture to form a rigid, self supporting structure.

9. A medical bandage according to claim 8, wherein said substrate comprises a knitted fabric having an extensibility of between 40 to 80 percent prior to being coated or impregnated with the reactive system.

10. A medical bandage according to claim 8 or 15, wherein the medical bandage is packaged until use in a sleeve comprising an aluminum foil laminate having an outer tear resistant layer, a central aluminum foil layer and an inner heat sealable plastic layer.

11. A medical bandage according to claim 10, wherein said elastomeric yarns are formed of fibers selected from the group consisting of synthetic elastomeric fibers and rubber.

12. A medical bandage according to claim 10, wherein said reactive system comprises a blended polyisocyanate, polyol, catalyst and stabilizer.

13. A medical bandage according to claim 8, wherein said substrate includes inelastic fibers selected from the group consisting of polypropylene and polyester.

14. A medical bandage according to claim 8, wherein said medical bandage is formed into a coil.

15. A medical bandage according to claim 14, and including a dispensing carton within which the coil of medical bandaging product is contained.

16. A medical bandage according to claim 8, wherein the elastomeric yarns are between 60–150 Decitex.

17. A medical bandage according to claim 8, wherein the elastomeric yarns are uncovered elastomeric yarns of between 60–150 Decitex.

18. An elongate medical bandaging product for being dispensed in lengths suitable for a given medical use, comprising:
  (a) an outer container formed of a moisture-impervious material and sealable to prevent entry of moisture, the container comprising an elongate product-dispensing sleeve having a moisture-proof sealable opening on one end and an enlarged product storage package communicating with the dispensing sleeve;
  (b) an elongate medical material positioned in the container in substantially moisture-free conditions and sealed therein against moisture until use, said medical material comprising:
    (I) a warn knitted substrate having a pair of opposed, major surfaces, said substrate comprising both elastomeric and inelastic yarns, said elastomeric yarns being present in the warp direction only and wherein the elastomeric and inelastic yarns each have about 48 to about 90 filaments;
    (ii) a reactive system impregnated into or coated onto said substrate, said system remaining stable when maintained in substantially moisture-free conditions and hardening upon exposure to sufficient moisture to form a rigid, self supporting structure; and
  (c) closure means for resealing the dispensing sleeve against entry of moisture after a predetermined length of the medical material has been dispensed for use to prevent hardening of the substrate remaining in the product container.

19. A medical bandaging product to claim 18, wherein said dispensing sleeve and said product storage package are integrally-formed.

20. A medical bandaging product to claim 18, and including a protective carton within which said product container is contained.

21. A medical bandaging product according to claim 18, 19 or 20, and wherein said elongate medical material is coiled within said storage package with an end portion thereof positioned in said product-dispensing sleeve for selective dispensing of desired lengths thereof.

* * * * *

UNITED STATES PATENT AND TRADEMARK OFFICE
CERTIFICATE OF CORRECTION

PATENT NO. : 6,974,430 B2
DATED : December 13, 2005
INVENTOR(S) : Evans, John C.

It is certified that error appears in the above-identified patent and that said Letters Patent is hereby corrected as shown below:

Title page,
Item [73], Assignee, should read -- BSN Medical, Inc. --

Column 10,
Line 41, delete "a" and insert -- an --.

Column 12,
Line 9, delete "warn" and insert -- warp --.
Line 29, add -- according -- after "product" and before " to".

Signed and Sealed this

Thirty-first Day of January, 2006

JON W. DUDAS
*Director of the United States Patent and Trademark Office*